US00PP28219P3

(12) United States Plant Patent
Zaiger et al.

(10) Patent No.: US PP28,219 P3
(45) Date of Patent: Jul. 25, 2017

(54) INTERSPECIFIC TREE NAMED 'FLAVOR BABY'

(50) Latin Name: **Interspecific *Prunus* species**
Varietal Denomination: Flavor Baby

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 118 days.

(21) Appl. No.: 14/756,859

(22) Filed: Oct. 23, 2015

(65) Prior Publication Data

US 2017/0118884 P1 Apr. 27, 2017

(51) Int. Cl.
*A01H 5/08* (2006.01)

(52) U.S. Cl.
USPC ..... Plt./180

(58) Field of Classification Search
USPC ..... Plt./156, 180
See application file for complete search history.

*Primary Examiner* — Susan McCormick Ewoldt
*Assistant Examiner* — Karen Redden

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Regular and productive bearer of medium size fruit.
3. Fruit with good flavor and eating quality.
4. Fruit with firm, red flesh.
5. Fruit with an attractive speckled red skin color.

1 Drawing Sheet

Botanical designation: Interspecific *Prunus* species.
Variety denomination: 'Flavor Baby'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

Prior Varieties

Among the existing varieties of interspecific trees, which are known to us, and mentioned herein, 'Coparose' Interspecific (U.S. Plant Pat. No. 20,173), 'Emerald Gem' Interspecific (U.S. Plant Pat. No. 14,599) and our proprietary non-patented interspecific seedling selections '22M650', '67Z2' and '20Z361'.

STATEMENT REGARDING FEDERALLY SPONSORED RESEARCH AND DEVELOPMENT

Not applicable.

ORIGIN OF THE VARIETY

The new and distinct interspecific tree was originated from crosses between *Prunus salicina* and *Prunus armeniaca*. The present variety was a selected seedling from a first generation cross between our proprietary non-patented interspecific variety '22M650' and 'Coparose' Interspecific (U.S. Plant Pat. No. 20,173). The non-patented interspecific seed parent (22M650) originated from a cross between our proprietary non-patented interspecific varieties '67Z2' and '20Z361'. A large number of these first generation seedlings were budded onto older established trees of 'Nemaguard' Rootstock (non-patented) to enhance earlier fruit production for evaluation. Under close and careful observation we recognized the desirable tree and fruit characteristics of the present seedling and selected it in 2010 for additional asexual propagation and commercialization.

ASEXUAL REPRODUCTION OF THE VARIETY

In 2010 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

A new and distinct variety of interspecific tree, which includes Plum and Apricot in its parentage, is of large size, vigorous, upright growth and is a regular and productive bearer of medium size fruit with good flavor and eating quality. The fruit is further characterized by having firm, red flesh and an attractive speckled red skin color. In comparison to its non-patented seed parent (22M650) the fruit of the new variety is larger in size and is approximately 8 days later in maturity. In comparison to its pollen parent 'Coparose' Interspecific (U.S. Plant Pat. No. 20,173) the fruit of the new variety has red flesh compared to yellow. In comparison to the commercial variety 'Emerald Gem' Interspecific (U.S. Plant Pat. No. 14,599) the fruit of the new variety has speckled red skin compared to yellow.

DESCRIPTION OF THE PHOTOGRAPH

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of Color published in 1958.

Tree:

*Size*.—Large, pruned to 3 to 3.5 meters in height and width for economical harvesting of fruit. Varies with different cultural practices.

*Vigor*.—Vigorous, tree growth of 1.5 to 2 meters the first growing season. Varies with cultural practices, soil type, fertility and climatic conditions.

*Form*.—Upright, usually pruned to vase shape.

*Branch habit*.—Upright, crotch angle approximately 35°, increases with heavy crop load.

*Productivity*.—Productive, thinning and spacing of fruit necessary for marketable size fruit. Number of fruit set varies with climatic conditions during blooming period.

*Bearer*.—Regular, has had adequate fruit set 4 consecutive years. No alternate bearing observed.

*Fertility*.—Self-sterile, pollinator required.

*Density*.—Medium dense, usually pruned to vase shape to increase air movement and sunlight to enhance fruit color and health of fruit spurs.

*Hardiness*.—Hardy in all stone fruit growing areas of California. Tree grown in USDA Hardiness Zone 9. Winter chilling requirement approximately 600 hours at or below 45° F.

Trunk:

*Size*.—Large, average circumference 50.8 cm at 25.4 cm above ground on a 6 year old tree.

*Stocky*.—Medium stocky.

*Texture*.—Medium shaggy, roughness increases with age.

*Color*.—Varies from 7.5YR 6/2 to 10YR 5/2.

Branches:

*Size*.—Medium. Average circumference 14.0 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 53 in a 25.8 square cm section of branch. Average length 4.4 mm. Average width 1.7 mm. Color varies from 5YR 2/4 to 5YR 3/2, varies with age of growth.

Leaves:

*Size*.—Medium. Average length 93.3 mm. Average width 43.3 mm.

*Form*.—Oblanceolate.

*Apex*.—Acuminate.

*Base*.—Cuneate.

*Margin*.—Doubly serrate.

*Thickness*.—Medium.

*Surface texture*.—Upper surface relatively smooth, slight indentations over midrib and leaf veins. Lower surface relatively smooth except for small ridges created by midrib and pinnate venation. Both upper and lower surfaces glabrous.

*Petiole*.—Average length 14.1 mm. Average width 1.5 mm. Longitudinally. grooved. Surface — glabrous. Color varies from 5GY 6/6 to 10R 2/6.

*Glands*.—Type — globose. Size — small. Average length 0.6 mm. Average diameter 0.4 mm. Number varies from 2 to 4, average number 3. Located primarily on base of leaf blade and upper portion of petiole. Color varies from 5GY 6/6 to 10R 2/6.

*Stipules*.—Average number 2. Average length 5.9 mm. Edges — pectinate. Color varies from 5GY 7/4 to 5GY 7/6.

*Color*.—Upper surface varies from 5GY 4/4 to 5GY 5/4. Lower surface varies from 5GY 3/4 to 7.5GY 3/4. Midvein color varies from 2.5GY 8/4 to 5GY 8/4.

Flower buds:

*Size*.—Medium to large. Average length 10.2 mm. Average diameter 5.6 mm.

*Hardiness*.—Hardy with respect to California winters.

*Density*.—Medium dense.

*Form*.—Conical, becoming elongated just before opening.

*Pedicel*.—Average length 5.7 mm. Average width 0.7 mm. Surface — glabrous. Color varies from 2.5GY 6/8 to 5GY 7/6.

*Color*.—N 9.5/(white).

*Number of buds per spur*.—Varies from 7 to 14, average number 10.

Flowers:

*Blooming period*.—Date of First Bloom Feb. 21, 2015. Date of Petal Fall Mar. 1, 2015, varies slightly with climatic conditions.

*Size*.—Medium to large. Average height 10.3 mm. Average diameter 19.1 mm.

*Petals*.—Number — normally 5, alternately arranged to sepals. Size — medium. Average length 9.4 mm. Average width 7.5 mm. Petal apex — rounded. Petal base — truncate. Form — globose. Arrangement — free to slightly overlapping. Margin — sinuate. Color N 9.5/(white). Both upper and lower surfaces glabrous.

*Sepals*.—Number — normally 5, alternately arranged to petals. Size — small to medium. Average length 2.5 mm. Average width 2.1 mm. Shape — ovate to triangular. Apex rounded to triangular. Margin — entire. Color — upper surface varies from 2.5GY 6/6 to 5GY 7/8. Lower surface varies from 2.5GY 6/8 to 5GY 6/8. Both upper and lower surfaces glabrous.

*Stamens*.—Average number per flower 38. Average filament length 7.3 mm. On average the stamens are above the height of the petals. Filament color N 9.5/(white). Anther color varies from 5Y 8.5/10 to 5Y 8/10.

*Pollen*.—Self-sterile, pollinator required. Color varies from 2.5Y 7/12 to 5Y 7/12.

*Pistil*.—Number — normally 1. Surface — glabrous. Average length 8.5 mm. Position of stigma an average of 1.0 mm below anthers. Color varies from 10Y 8.5/4 to 2.5Y 8/8.

*Fragrance*.—Moderate aroma.

*Color*.—N 9.5/(white).

*Pedicel*.—Average length 6.2 mm. Average width 0.7 mm. Color varies from 10Y 6/8 to 2.5GY 6/8.

*Number flowers per flower bud*.—Average number 2, varies from 1 to 3.

Fruit:

*Maturity when described*.—Firm ripe and ready for consumption.

*Date of first picking*.—Jul. 1, 2015.

*Date of last picking*.—Jul. 10, 2015, varies slightly with climatic conditions.

*Size*.—Medium. Average diameter axially 47.3 mm. Average transversely in suture plane 61.4 mm. Average weight 119.3 grams, varies slightly with fertility of the soil, amount of thinning. and climatic conditions.

*Form*.—Globose.

*Suture*.—Slightly lipped, some fruit with slight suture.

*Ventral surface*.—Nearly smooth.

*Apex*.—Slightly retuse.

*Base*.—Flat.

*Stem cavity*.—Rounded to slightly elongated in suture plane. Average depth 8.6 mm. Average diameter 5.2 mm.

Stem:

*Size*.—Medium. Average length 12.0 mm. Average diameter 2.5 mm.

*Color*.—Varies from 7.5YR 3/4 to 10YR 3/6.

Flesh:

*Ripens*.—Evenly.

*Texture*.—Firm, meaty.

*Fibers*.—Few, small, tender.

*Firmness*.—Firm, comparable to commercial interspecific varieties.

*Aroma*.—Wanting.

*Amydgalin*.—Undetected.

*Eating quality*.—Good.

*Flavor*.—Good, with a good balance between acid and sugar.

*Juice*.—Slight amount, enhances flavor.

*Acidity*.—Not available.

*Brix*.—Average brix 16.0°, varies slightly with amount of fruit per tree and climatic conditions.

*Color*.—Varies from 5R 3/10 to 7.5R 2/6.

*Pit cavity*.—Average length 23.1 mm. Average width 18.9 mm. Average depth 6.2 mm. Color varies from 5R 2/4 to 7.5R 2/4.

Skin:

*Thickness*.—Medium.

*Surface*.—Smooth.

*Bloom*.—Moderate amount, complete coverage.

*Tendency to crack*.—None.

*Color*.—Ground color varies from 10Y 7/4 to 10Y 7/6. Overspread with 7.5R 2/6 to 7.5R 2/8. Very small, randomly spaced areas of exposed ground color giving a speckled pattern to the surface.

*Tenacity*.—Tenacious to the flesh.

*Astringency*.—Undetected.

Stone:

*Type*.—Clingstone, medium adherence to flesh.

*Size*.—Medium. Average length 22.1 mm. Average width 17.9 mm. Average thickness 10.4 mm.

*Form*.—Obovoid.

*Base*.—Flat.

*Apex*.—Pointed. Average length 1.3 mm.

*Surface*.—Slightly pitted throughout, pits vary from rounded to slightly elongated.

*Sides*.—Unequal, one side extending further from suture plane.

*Ridges*.—A small, narrow ridge on each side of suture extending from base to apex.

*Tendency to split*.—None.

*Color*.—Varies from 7.5YR 5/6 to 7.5YR 5/8 when dry.

Kernel:

*Size*.—Medium. Average length 14.6 mm. Average width 10.2 mm. Average depth 6.0 mm.

*Form*.—Ovate.

*Viability*.—Viable, complete embryo development.

*Skin color*.—Varies from 5Y 9/4 to 7.5Y 9/4.

Use: Dessert. Market — local and long distance.

Keeping quality: Good, held firm in cold storage for 3 weeks at 38° to 42° F. without internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices. The present new variety of interspecific tree, its flowers foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

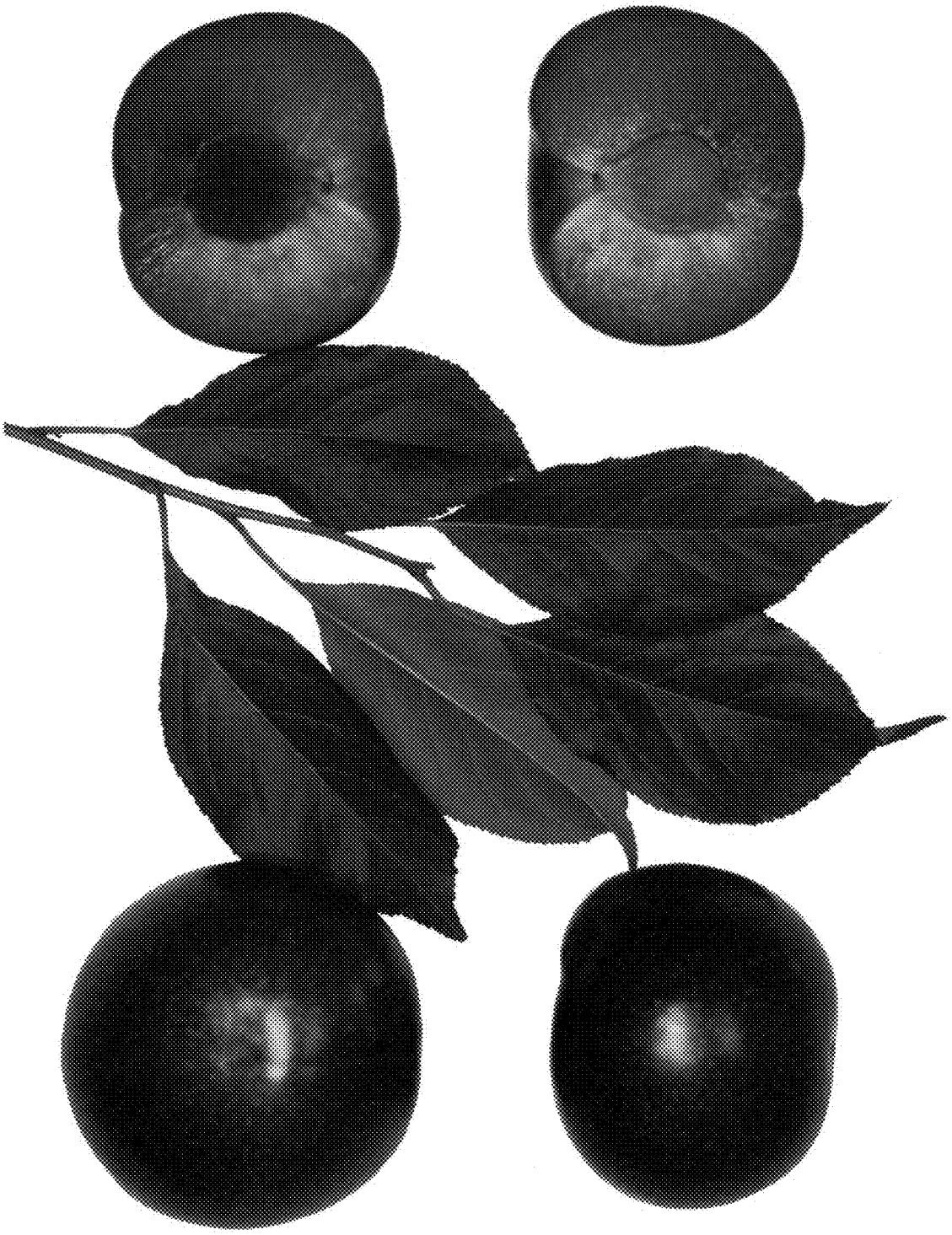

* * * * *